United States Patent [19]

Beckstein

[11] Patent Number: 4,696,185
[45] Date of Patent: Sep. 29, 1987

[54] METHOD AND APPARATUS FOR CONTROLLING THE DYE RECEPTIVITY OF TEXTILES

[75] Inventor: Hellmut Beckstein, Bad Abbach, Fed. Rep. of Germany

[73] Assignee: Mahlo GmbH +Co. KG., Donau, Fed. Rep. of Germany

[21] Appl. No.: 603,605

[22] Filed: Apr. 25, 1984

[30] Foreign Application Priority Data

May 4, 1983 [DE] Fed. Rep. of Germany ....... 3316171

[51] Int. Cl.$^4$ ........................................... G01N 33/36
[52] U.S. Cl. .................................................. 73/37.7
[58] Field of Search .......................... 73/37.7, 37.6, 38

[56] References Cited

U.S. PATENT DOCUMENTS 3,201,985  8/1965  Williams ........................... 73/37.7 X
3,218,844  11/1965  Kleist et al. ...................... 73/37.6 X
4,253,010  2/1981  Brown et al. ....................... 73/38 X
4,311,037  1/1982  Gotchel et al. ................... 73/37.7 X

FOREIGN PATENT DOCUMENTS 2655973  12/1977  Fed. Rep. of Germany .
 980058  1/1965  United Kingdom ..................... 73/38
 993621  6/1965  United Kingdom ................... 73/37.7
 430310  5/1975  U.S.S.R. ............................... 73/37.7

Primary Examiner—Stewart J. Levy
Assistant Examiner—Joseph W. Roskos
Attorney, Agent, or Firm—W. G. Fasse; D. H. Kane, Jr.

[57] ABSTRACT

For controlling the dye receptivity or color absorption capacity of textile goods by means of air or sound, a web is continually guided between transmitter and receiver, and measured values determined at various locations of the web are compared with each other.

8 Claims, 2 Drawing Figures

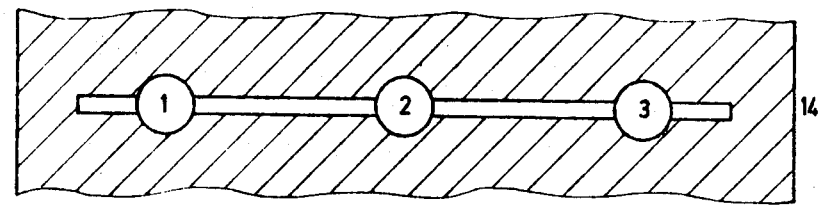
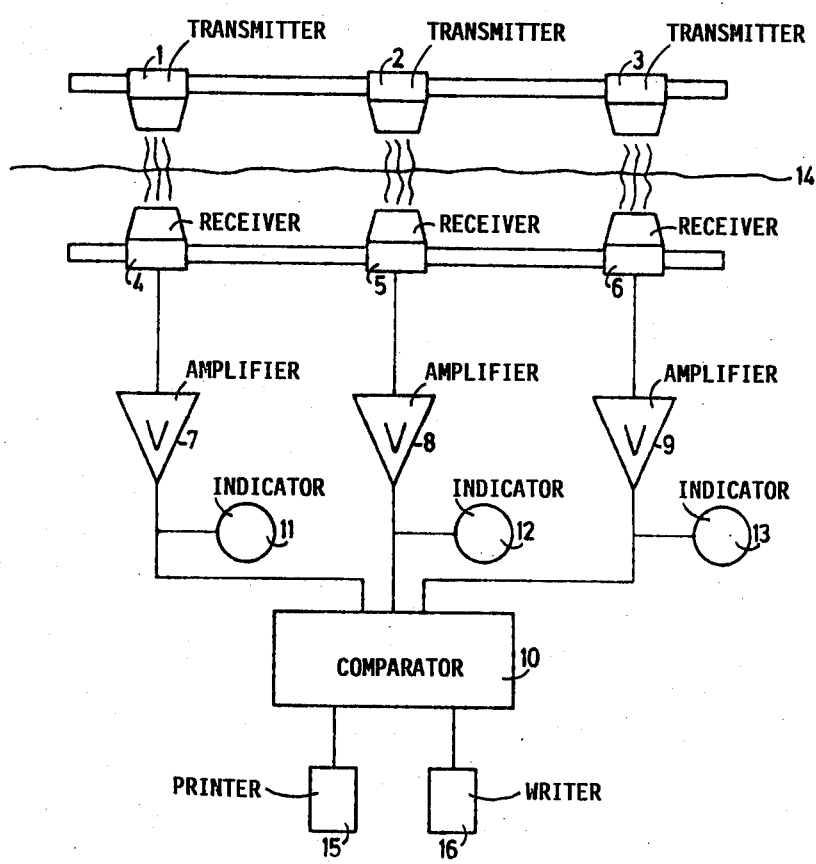

METHOD AND APPARATUS FOR CONTROLLING THE DYE RECEPTIVITY OF TEXTILES

DESCRIPTION OF THE PRIOR ART

A large problem which is decisive for the loss of quality, in the dyeing of textiles, is the non-uniform color distribution over the width and length of the pieces to be dyed. Color or dye variations, so-called color or dye run-offs, between the middle of the web and the edge zones are not rare. Similarly, such variations also frequently occur between the beginning and end of a textile web. In the manufacture of ready-to-wear clothing made of such colored articles, such color deviations then arise as unacceptable color variations, for instance, within a piece of clothing.

Dyeing errors of this type can have various causes. Depending on the dyeing method employed, machine or technical errors, operator's errors, and especially non-uniformities in the raw goods are possible. One cause for color or dye run-offs is the application of varying amounts of dye liquor onto the textile goods arising for instance, due to a non-uniform squeezing-out of the goods. Thus, there are devices known which allow controlling the amount of water distributed across the width of the goods, for example, with the aid of moisture measuring devices according to the microwave-absorption method (German Patent (DE-PS) 2,655,973). In order to monitor the color uniformity, colorimetric measuring devices have also been developed, which allow the colors to be objectively measured directly on the running web of goods, but of course, only after the drying of the dye.

The measurement of the distribution of the watery color dye liquor and the possible regulation or control of this distribution however takes into consideration only one of the many causes for the color non-uniformities, and at that—as is shown by the experiences of dyers—not even the decisive cause. On the other hand, the raw goods themselves frequently include peculiarities, which cause a varying dye liquor absorption. Such peculiarities include, for example, a non-uniform weight per surface area, but also above all, non-uniform dye absorption characteristics, caused, for example, by fluctuations in the structure of the textile, by the fiber roughness, by the size and distribution of the capillaries between the fibers, by the hygroscopic behavior dependent thereon, and the like.

It is therefore very important for the dyer to know the color absorption or dye receptivity characteristics of a supplied undyed piece, already before the dyeing, so that especially nonuniform batches will, from the start, not be provided for a single color dyeing, for instance. Such pieces may on the other hand, be useful for printing or for other purposes, in which color run-offs do not play an important roll.

OBJECTS OF THE INVENTION

It is therefore the object of the invention to provide a method and apparatus for the control of textiles, by means of which rejects of the textile goods due to color variations, may be avoided without damage to the textiles. This object is achieved by the features of the claims.

SUMMARY OF THE INVENTION

The invention is based on the recognition that a relation exists between the dye receptivity of textiles and the permeability thereof. Varying permeabilities of a web of goods with respect to air or sound, cause respective non-uniform color or dye distributions, whereby such permeability variations are not necessarily based on variations in the weight per surface area. Rather, more often such permeability variations are caused by differences in the structure of the textiles, which are apparent in the number, type, shape and size of the interstitial spaces or capillaries between the fibers and on the spaces between the threads, in the appearance of the surface of the yarns, and similar mechanical textile characteristics. The causes for such differences may be found in the material production e.g. weaving or knitting as well as already in the yarns themselves which are used to make the fabric.

For the purpose of controlling, according to the invention, the dyeability of textiles, air or sound energy is applied to the textile at one or several locations on the web at the edges or the center thereof, by means of one or several measuring heads traversing across the web, or by means of band-shaped measuring systems which reach across the entire width. The amount or quantity of the energies passing through the textile is measured with the aid of appropriate receivers. This measuring may be achieved with receivers for air through flow, air pressure, or for sound amplitudes. The signals measured at the various locations of the web are compared with each other in a comparator arrangement; a computer can calculate the percentile deviations, a printer or a writing-recorder can record the uniformity.

The measurement may, however, also be achieved by means of reflection, in that the air reflected by the web of goods is measured. That is, the pressure of the air directed onto the web of goods, or rather the back pressure caused by the web of goods, is controlled with the measuring device arranged on one side of the web. A measuring device on the other side of the web of goods is then no longer necessary. Also, in controlling air sucked through the web of goods, a measuring device is only required on one side of the web of goods.

Measuring the permeability or the flow resistance of textile goods with respect to air is known as such, and so is measuring the water permeability of rain clothing and the air resistance of parachute silk. These measurements, however, are carried out with the sample kept stationary, so that it is not possible thereby to determine variations of the permeability over a large surface.

BRIEF FIGURE DESCRIPTION

In order that the invention may be clearly understood, it will now be described, by way of example, with reference to the accompanying drawings, wherein:

FIG. 1 shows a top view and

FIG. 2 shows schematically a sectional view of the measuring arrangement for measuring the dye receptivity characteristics of the goods.

DETAILED DESCRIPTION OF PREFERRED EXAMPLE EMBODIMENTS AND OF THE BEST MODE OF THE INVENTION

Sound energy (ultrasonic energy) is produced in the transmitters 1 to 3 and is radiated onto the web of goods 14. The receivers 4 to 6 may be (sound) pressure measurement sensors, which convert the energies passing through the textile into electric signals. The received energies are compared to their respective transmitted energies. The damping is determined by the comparing.

The damping is a measure of the permeability of the goods being tested and of the dye receptivity of the goods. Additionally, the dampings of the three sections (1-4, 2-5, and 3-6) are compared with each other in a circuit 10, in order to determine non-uniformities in the permeability. Finally, the permeability of the test goods is indicated at three locations (middle and both edges) by the indicators 11, 12, and 13. Simultaneously, the permeability may be printed at 15 or it may be written at 16. The printer or writer outputs are for example, passed on with the textile pieces as data for the dying. 7, 8, and 9 are amplifiers.

For achieving the purpose of the invention only relative measured values, or the comparison relative to a prescribed standard over the length of the web, are necessary. Therefore, only sufficiently similar measuring arrangements are required, not however, reproduceable absolute, measured values. The choice of the measuring medium to use depends upon the conditions and characteristics of the textile goods to be tested. However, such conditions and characteristics may vary considerably. Thus, tightly-woven and substantially non-transparent textiles are tested with air or sound as a medium.

Due to the required uniformity of the characteristics of the individual measuring sections, it may be recommendable under certain circumstances to use a single measuring device, which is moved across the web for producing a non-interrupted profile of the permeability ratios or characteristics. It is also conceivable to use two or more measuring devices moving symmetrically relative to the middle of the web, whereby the signals, from these measuring devices are compared constantly with each other in pairs.

Although the invention has been described with reference to specific example embodiments, it will be appreciated, that it is intended to cover all modifications and equivalents within the scope of the amended claims.

I claim:

1. A method for preparing a record of the dye receptivity characteristics of an undyed web of textile for the subsequent use by a dyer when dyeing said web, comprising the following steps:
   (a) running said undyed web of textile through a measuring station including mechanical energy transmitter means and mechanical energy receiver means,
   (b) applying mechanical energy to said undyed web of textile by said transmitter means,
   (c) measuring mechanical energy passed through or reflected by said undyed web,
   (b) comparing the applied mechanical energy with the measured mechanical energy for determining said dye receptivity of said undyed web of textile,
   (d) comparing mechanical energies measured at different locations in said undyed web of textile with each other for determining non-uniformities in said dye receptivity, and
   (f) recording said non-uniformities in said dye receptivity to form said record for said subsequent use by the dyer for dyeing said undyed web of textile.

2. The method of claim 1, wherein said applying of mechanical energy involves pressing air onto said undyed web of textile.

3. The method of claim 1, wherein said applying of mechanical energy involves sucking air through said undyed web of textile.

4. The method of claim 1, wherein said applying of mechanical energy involves transmitting sound energy through said undyed web of textile.

5. The method of claim 1, wherein said applying of mechanical energy involves transmitting ultra-sound energy through said undyed web of textile.

6. An apparatus for producing a record of the dye receptivity characteristics of an undyed web of textile for the subsequent use by a dyer for dyeing said undyed web, comprising a measuring station through which said undyed web is moving, mechanical energy transmitter means located for applying mechanical energy to said undyed web of textile, receiver means located for measuring mechanical energy passed through or reflected by said undyed web, means for comparing applied mechanical energy with measured mechanical energy for determining said dye receptivity of said undyed web of textile, means for comparing measured mechanical energies measured at different locations in said undyed web of textile with each other for determining non-uniformities in said dye receptivity, and means for recording said non-uniformities in said dye receptivity to form said record for said subsequent use by the dyer for dyeing said undyed web of textile.

7. The apparatus of claim 6, wherein said mechanical energy transmitter means comprise at least one transmitter on one side of said undyed web of textile and wherein said receiver means comprise at least one receiver located opposite the respective transmitter on the other side of said web of textile, said transmitter and said receiver being movable across and perpendicularly to the length of said undyed web of textile.

8. The apparatus of claim 6, wherein said mechanical energy transmitter means and said mechanical energy receiver means comprise two or more even numbered transmitters and receivers which are movable back and forth symmetrically relative to the middle of the undyed web.

* * * * *

UNITED STATES PATENT AND TRADEMARK OFFICE
CERTIFICATE OF CORRECTION

PATENT NO. : 4,696,185
DATED : September 29, 1987
INVENTOR(S) : Hellmut Beckstein It is certified that error appears in the above-identified patent and that said Letters Patent is hereby corrected as shown below:

On the title page in [73] the Assignee's address should read as follows:

-- Saal/Donau, Fed. Rep. of Germany--.

Claim 1, column 4, line 1, "( b)" should be --(d)--.
Claim 1, column 4, line 4, "( d)" should be --(e)--.

Signed and Sealed this

Twelfth Day of April, 1988

Attest:

DONALD J. QUIGG

*Attesting Officer*  *Commissioner of Patents and Trademarks*